US00PP18986P2

(12) United States Plant Patent
Hanes

(10) Patent No.: US PP18,986 P2
(45) Date of Patent: Jun. 24, 2008

(54) ***VERBENA* PLANT NAMED 'LAN REDA07'**

(50) Latin Name: *Verbena hybrida*
Varietal Denomination: Lan Redo07

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/709,582

(22) Filed: Feb. 22, 2007

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent L Bell
(74) *Attorney, Agent, or Firm*—Jondle & Associates, P.C.

(57) ABSTRACT

A *verbena* cultivar particularly distinguished by its red-colored flowers with vigorous and free-branching multiple secondary lateral branches, low and outwardly spreading growth habit, and tolerance to powdery mildew is disclosed.

1 Drawing Sheet

Genus and species: *Verbena hybrida.*
Variety denomination: 'Lan Reda07'.

BACKGROUND OF THE NEW PLANT

The present invention comprises a new and distinct cultivar of *verbena,* botanically known as *Verbena hybrida,* and hereinafter referred to by the cultivar name 'Lan Reda07'. The new cultivar originated in 2004 in Gilroy, Calif. from an hybridization of female parent 'Lan Redtwo' (U.S. Plant Pat. No. 17,842), with red flowers, and male proprietary line '1579-2' (unpatented), having a purple flower color with an eye.

The seeds produced by the pollination were sown in June 2004. A single plant selection was chosen for further evaluation and for asexual propagation in September 2004.

The new cultivar was created in 2004 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar have been applied for in Switzerland on Oct. 30, 2006.

SUMMARY OF THE INVENTION

The following are the most outstanding and distinguishing characteristics of the new cultivar when grown under normal horizontal practices in Gilroy, Calif. and Andijk, The Netherlands.

1. Red flower color;
2. Low and outwardly spreading growth habit;
3. Vigorous and free branching with multiple secondary lateral branches; and
4. Tolerance to powdery mildew.

DESCRIPTION OF PHOTOGRAPHS

This new *verbena* plant is illustrated by the accompanying photographs which show overall plant habit, including blooms, buds and foliage of 18 to 22 week-old plants. The plants were grown in a greenhouse before being moved outside in Andijk, The Netherlands during the summer months. The photographs were taken in August 2005. The colors shown are as true as can be reasonably obtained by conventional photographic procedures.

Figure 1:
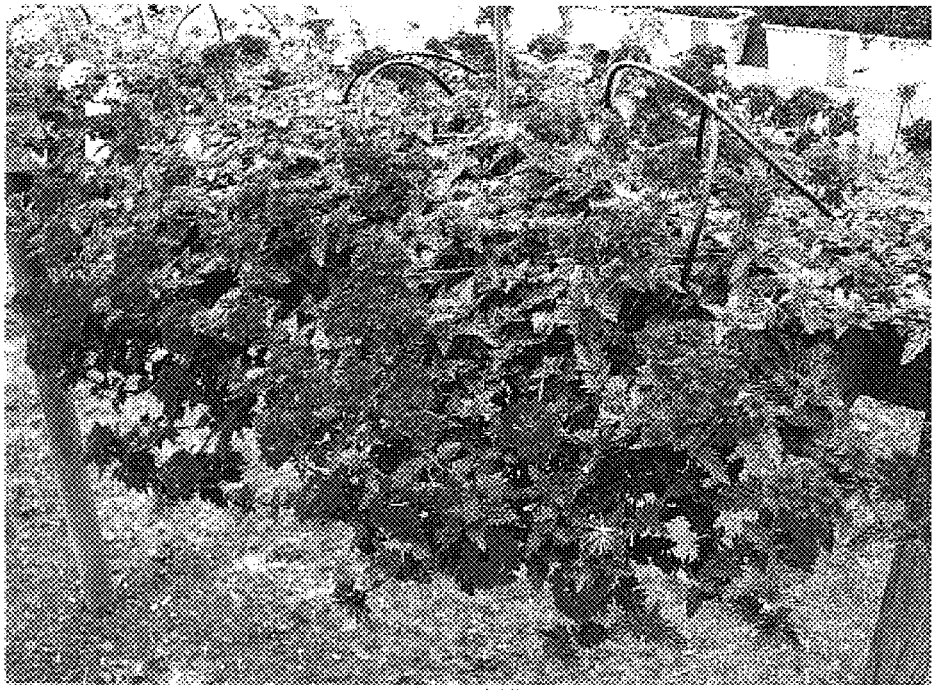

FIG. 1. shows the overall plant habit, including blooms, buds and foliage of the plant.

Figure 2:
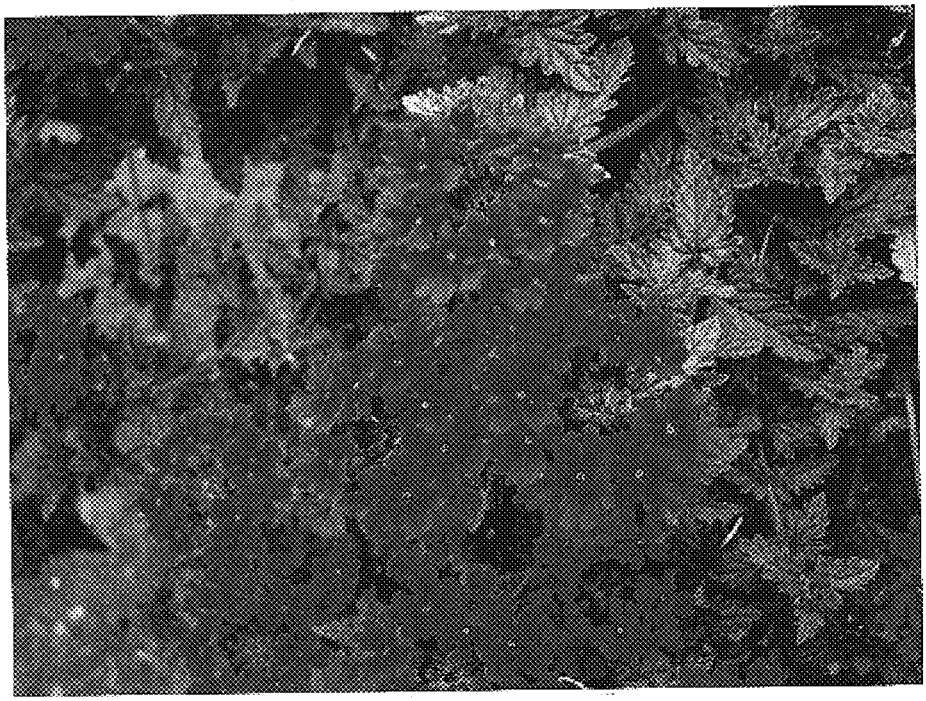

FIG. 2. shows a close-up of mature inflorescences of the plant.

DESCRIPTION OF THE NEW CULTIVAR

The following detailed descriptions set forth the distinctive characteristics of 'Lan Reda07'. The data which define these characteristics were collected from asexual reproductions carried out in Gilroy, Calif. The plant history was taken from plants approximately 20–24 weeks old, grown in 6-inch pots, in Gilroy, Calif. in the summer season. The plants had one plant growth regulator treatment and one terminal pinch after cuttings were transplanted to 4-inch pots and then to 6-inch pots. Color readings were taken in a LEXAN-covered greenhouse in summer under natural light. Color references are primarily to the R.H.S. Colour Chart of The Royal Horticultural Society of London (RHS) (2001 edition). Texture description details were observed with a dissecting microscope.

DETAILED BOTANICAL DESCRIPTION

Classification:
*Botanical.—Verbena hybrida.*
*Common name.—Verbena.*

Parentage:
*Female.*—'Lan Redtwo' (U.S. Plant Pat. No. 17,842), with red flowers.
*Male.*—'1579-2' unpatented proprietary line having purple colored flowers with an eye.

Growth:

*Form.*—Low and outwardly spreading and decumbent habit.

*Growth and branching habit.*—Vigorous and free-branching with multiple secondary lateral branches.

*Height* (*measured from the top of the soil, including flowers*).—8.0 cm to 10.0 cm.

*Width* (*horizontal plant diameter*).—35.0 cm to 40.0 cm.

*Time to produce a finished flowering plant.*—Approximately 10 weeks for a 12-cm pot in the spring.

*Outdoor plant performance.*—Use in containers and hanging baskets.

*Time to initiate and develop roots.*—Approximately 7 to 10 days at 22 to 24 degrees Celsius.

*Root description.*—Fibrous, fleshy, white.

Leaves:

*Arrangement.*—Opposite.

*Immature leaf.*—Color: Upper surface: Closest to RHS 137A. Lower surface: Between RHS 137B and RHS 137C.

*Mature leaf.*—Color: Upper surface: Closest to RHS 137A. Lower surface: Closest to RHS 137B. Length: 4.0 cm to 4.7 cm. Width: 3.0 cm to 3.3 cm. Shape: Ovate. Apex: Acute. Base: Attenuate. Margin: Broadly crenate to slightly cleft. Texture: Hirsute. Venation: Pinnate. Venation color: RHS 145B.

*Petioles.*—Length: 0.3 cm to 1.0 cm. Diameter: 0.15 cm to 0.2 cm. Color: RHS 137A. Texture: Hirsute.

Stems:

*Number of branches per plant.*—Approximately 20.

*Color.*—RHS 144A.

*Length.*—20.0 cm to 23.0 cm.

*Diameter* (*measured from the midpoint*).—0.2 cm to 0.25 cm.

*Internode length.*—2.8 cm to 3.0 cm.

*Texture.*—Hirsute and glandular hairs, some with a magenta hue.

*Stem anthocyanin.*—Absent.

Flower buds:

*Color* (*at tight bud*).—Closest to RHS 46A.

*Shape.*—Linear.

*Diameter.*—0.25 cm to 0.3 cm.

*Length.*—1.7 cm to 2.0 cm.

Inflorescence:

*Blooming habit.*—Flowers continuously from spring through fall.

*Lastingness and individual blooms on the plant.*—5 to 7 days.

*Fragrance.*—None.

*Inflorescence type.*—Terminal raceme.

*Horizontal diameter of inflorescence.*—5.0 cm to 5.5 cm.

*Vertical diameter of inflorescence.*—4.5 cm to 5.5 cm.

*Number of florets per raceme.*—18 to 26.

*Peduncle.*—Color: Closest to RHS 144A. Diameter: 0.2 cm. Length: 4.7 cm to 7.0 cm. Texture: Hirsute; glandular hairs, some with magenta-red hue Flowers:

*Floret form.*—Salverform; sessile on spikes.

*Diameter.*—1.8 cm to 2.2 cm.

*Number of petals and arrangement.*—Each floret is composed of 5 petals fused at the base.

*Immature flower.*—Color: Upper surface: Closest to RHS 46B base color with RHS 46A basally around corolla opening. Lower surface: RHS 46B; basally RHS N155D but whiter.

*Mature flower.*—Color: Upper surface: RHS 46C base color and RHS 46B around the corolla opening; with some slight irregular patches of RHS 46A hues. Lower surface: RHS 47C; RHS 45C at the margins; basally RHS N155D but whiter. Corolla: Tube color (inside): RHS 4D. Tube color (outside): RHS 2D. Tube length: 2.0 cm to 2.2 cm.

*Petals.*—Size: Length: 0.7 cm to 0.9 cm. Width: 0.5 cm to 0.7 cm. Lobe shape: Obovate. Apex: Emarginate. Base: Fused. Margin: Entire. Texture: Upper surface: Papillose. Lower surface: Pilose; papillose.

*Calyx.*—Sepals: Five sepals whose margins are fused to each other along their length, with a transparent membrane of less than 0.1 cm in width and with one smaller sepal attached to the base of the calyx General color: Between RHS 143A and RHS 143B for the outer surface; inner surface was not observed. Length: 1.3 cm to 1.4 cm. Width: 0.1 cm. Shape: Linear. Apex: Acute. Base: Fused. Margin: Entire. Texture: Very hirsute; glandular hairs, most have a magenta hue.

Reproductive organs:

*Stamens.*—Anthers and filaments are fused to the upper half of the corolla tube.

*Anther quantity.*—Four with two pollen sacs per anther.

*Anther length.*—0.05 cm to 0.1 cm.

*Pollen.*—Amount: Moderate. Color: RHS 1A.

*Pistil.*—1.

*Style length.*—1.7 cm to 1.8 cm.

*Style color.*—RHS 145D.

*Stigma color.*—RHS 143C.

Fruit/Seed set: Have not been produced.

Disease and insect resistance: Tolerant to powdery mildew.

COMPARISON WITH PARENTAL AND COMMERCIAL CULTIVARS

'Lan Reda07' differs from the female parent 'Lan Redtwo' (U.S. Plant Pat. No. 17,842) in that 'Lan Reda07' is more compact, has less pinnatisect foliage and slightly larger foliage that 'Lan Redtwo'.

'Lan Reda07' differs from the male parent, proprietary line '1579-2' (unpatented) in that 'Lan Reda07' is more compact, has red-colored flowers and is more floriferous, while '1579-2' has a purple flower color.

'Lan Reda07' differs from the commercial variety 'Lan Chered' (U.S. Plant Pat. No. 15,602) in that 'Lan Reda07' has longer stems and internodes, less branching and lighter green, smaller leaves that 'Lan Chered'. Additionally, 'Lan Reda07' also has a velvety red flower color, while 'Lan Chered' has a more cherry-red flower color.

I claim:

1. A new and distinct cultivar of *verbena* plant as shown and described herein.

* * * * *